US012589047B2

(12) United States Patent
Carr et al.

(10) Patent No.: US 12,589,047 B2
(45) Date of Patent: Mar. 31, 2026

(54) CATCHER'S KNEE EXOSKELETON

(71) Applicant: REGENTS OF THE UNIVERSITY OF MICHIGAN, Ann Arbor, MI (US)

(72) Inventors: Austin Carr, Lisle, IL (US); Christopher Colón, New York, NY (US); Matthew Rudy, Ann Arbor, MI (US); John Ike Smith, Washington, NJ (US); Alex Turk, Canton, MI (US); Elliott J. Rouse, Ann Arbor, MI (US); William Grundfest, Los Angeles, CA (US); Zachary Grundfest, Los Angeles, CA (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 539 days.

(21) Appl. No.: 18/128,108

(22) Filed: Mar. 29, 2023

(65) Prior Publication Data

US 2023/0310250 A1 Oct. 5, 2023

Related U.S. Application Data

(60) Provisional application No. 63/326,017, filed on Mar. 31, 2022.

(51) Int. Cl.
A61H 1/02 (2006.01)
A61F 5/01 (2006.01)
(Continued)

(52) U.S. Cl.
CPC ........... A61H 1/024 (2013.01); A61F 5/0123 (2013.01); B25J 9/0006 (2013.01); B25J 13/088 (2013.01);
(Continued)

(58) Field of Classification Search
CPC ...... A61H 1/024; A61F 5/0123; B25J 9/0006; B25J 13/088; A63B 2069/0011
See application file for complete search history.

(56) References Cited

U.S. PATENT DOCUMENTS

| | | | |
|---|---|---|---|
| 10,966,894 B2 * | 4/2021 | Tung ...................... | A61H 1/024 |
| 2007/0010772 A1 * | 1/2007 | Ryan ..................... | A61F 5/0123 |
| | | | 602/26 |

(Continued)

FOREIGN PATENT DOCUMENTS

| | | |
|---|---|---|
| CN | 205988396 U | 3/2017 |
| EP | 2842527 A1 | 3/2015 |

(Continued)

OTHER PUBLICATIONS

Translation KR 20160120835.*

(Continued)

*Primary Examiner* — Shaun R Hurley
(74) *Attorney, Agent, or Firm* — MARSHALL, GERSTEIN & BORUN LLP

(57) ABSTRACT

The present disclosure provides an exoskeleton mechanism for supporting a joint. The exoskeleton mechanism includes a brace having a first arm and a support arm, the support arm pivotably connected to the first arm. The exoskeleton mechanism further includes a spring secured to the first arm, the spring having a first length at an equilibrium position and a second length at a displaced position, a spring force generated by the spring when the spring is in the displaced position. Additionally, the exoskeleton mechanism has a cable having a first end and a second end, the first end coupled to the support arm and the second end coupled to the spring such that rotation of the support arm relative to the first arm causes the spring to move to the displaced position and the spring force is transferred to the support arm.

15 Claims, 11 Drawing Sheets

(51) Int. Cl.

| | | |
|---|---|---|
| B25J 9/00 | (2006.01) | |
| B25J 13/08 | (2006.01) | |
| *A63B 71/12* | (2006.01) | |

(52) U.S. Cl.

CPC .................. *A61F 2005/0197* (2013.01); *A61H 2201/1207* (2013.01); *A61H 2201/1253* (2013.01); *A61H 2201/1642* (2013.01); *A61H 2201/1676* (2013.01); *A61H 2201/5007* (2013.01); *A61H 2201/5084* (2013.01); *A61H 2203/0418* (2013.01); *A63B 2071/125* (2013.01)

(56) References Cited

U.S. PATENT DOCUMENTS

| | | | | |
|---|---|---|---|---|
| 2011/0251534 | A1 | 10/2011 | Matsuoka | |
| 2013/0006159 | A1 | 1/2013 | Nakashima et al. | |
| 2014/0276265 | A1* | 9/2014 | Caires ................. | A61H 1/0255 601/34 |
| 2015/0005686 | A1* | 1/2015 | Kazerounian ......... | A61F 5/0123 602/16 |
| 2018/0133905 | A1* | 5/2018 | Smith ..................... | F16D 25/14 |
| 2019/0060157 | A1* | 2/2019 | Lamb ..................... | B25J 9/0006 |
| 2021/0077288 | A1 | 3/2021 | Shimada | |

FOREIGN PATENT DOCUMENTS

| | | | | |
|---|---|---|---|---|
| EP | 3241531 | A1 | 11/2017 | |
| EP | 3326759 | A1 | 5/2018 | |
| KR | 20160120835 | A * | 10/2016 | ........... B25J 9/0006 |
| WO | WO-2010/011848 | A1 | 1/2010 | |
| WO | WO-2019057797 | A1 * | 3/2019 | ............. B25J 9/104 |
| WO | WO-2022006384 | A1 * | 1/2022 | ............. A61H 1/024 |

OTHER PUBLICATIONS

ExoPower Knee Brace, Retrieved from the Internet at https://www.amazon.com/Boosters-Stabilizer-Suitable-Compression-Climbing/dp/B08K42D9JK/ref=sr_1_3?crid=2OQXGH3JX6G6E&keywords=knee+protection+booster%2C+knee+brace+joint+support+spring+knee&qid=1647870813&sprefix=knee+protection+booster%2C+knee-+brace+joint +support-+spring+knee%2Caps%2C89&sr=8-3 (Mar. 28, 2023).

ROM Knee Brace, Retrieved from the Internet at https://cdn.shopify.com/s/files/1/0763/4541/files/rom_hinged_knee_brace_manual.pdf?5256 (Mar. 28, 2023).

Breg Axiom-D Elite Athletic Sport Brace, Retrieved from the Internet at https://www.healthproductsforyou.com/p-breg-axiom-d-elite-athletic-sport-knee-brace.html (Mar. 28, 2023).

Mumian 3D Pressurized Support Brace, Retrieved from the Internet at https://www.allexpress.com/item/32818722010.html?spm=a2q0o.detail.1000023.3.61c46265jXnBI2 (Mar. 28, 2023).

Immobilizer Knee Brace, Retrieved from the Internet at https://www.amazon.com/United-Ortho-61016-3-Panel-Immobilizer/dp/B07K6SGPBV/ref=sr_1_5?adgrpid=1342504259719515&hvadid=83906755411344&hvbmt=be&hydev=c&hvlocphy=97755&hvnetw=o&hvomt=e&hytargid=kwd-83906855160566%3Aloc-190&hydador=21879_13322005&keywords=immobilizer+kneeαbrace&qid=1647868438&sr=8-5 (Mar. 28, 2023).

Easton Knee Saver, Retrieved from the Internet at https://www.amazon.com/Easton-Knee-Saver-Black-Large/dp/B0000AQI4B/ref=sr_1_3?adorpid=1331509144842913&hvadid=83219392526795&hvbmt=be&hvdev=c&hvlocphy=97755&hvnetw=o&hvqmt=e&hvtargid=kwd-83219665489795%3Aloc-190&hydadcr=16038_10547218&keywords=knee+saver+easton&qid=1647868802&sr=8-3 (Mar. 28, 2023).

International Application No. PCT/US2023/016742, International Search Report and Written Opinion, mailed Oct. 18, 2023.

* cited by examiner

800

814

832

824

816

822

826

912

828

812

CATCHER'S KNEE EXOSKELETON

RELATED APPLICATIONS

The application claims the benefit of the filing date of U.S. Provisional Application No. 63/326,017, filed Mar. 31, 2022, entitled, "Catcher's Knee Exoskeleton." The entire text of U.S. Provisional Application No. 63/326,016 is incorporated by reference.

FIELD OF DISCLOSURE

The present disclosure relates to external joint support mechanisms, and, more particularly, to a catcher's knee exoskeleton.

BACKGROUND

Baseball catchers stand and crouch behind home plate and the baseball batter to catch a baseball if the batter fails to hit a baseball pitched by a baseball pitcher. The catcher maintains the crouch position for extended periods of time during the game. Athletes in other sports maintain a similar crouching position for extended periods of time (e.g., catchers in softball, wicketkeepers in cricket, ball persons in tennis, etc.).

Extended periods of time in a crouching position can cause strain on a person's knees. Further, these sports also typically require the crouching athlete to quickly launch from the crouching position to run or sprint away. In some cases, the strain of extended crouching or running from a crouching position can result in knee injuries that inhibit the athlete's ability to play or enjoy the sport.

SUMMARY

In one aspect, the present disclosure provides an exoskeleton mechanism for supporting a joint. The exoskeleton mechanism includes a brace having a first arm and a support arm, the support arm pivotably connected to the first arm. The exoskeleton mechanism further includes a spring secured to the first arm, the spring having a first length at an equilibrium position and a second length at a displaced position, a spring force generated by the spring when the spring is in the displaced position. Additionally, the exoskeleton mechanism has a cable having a first end and a second end, the first end coupled to the support arm and the second end coupled to the spring such that rotation of the support arm relative to the first arm causes the spring to move to the displaced position and the spring force is transferred to the support arm.

In some variations, the spring of the exoskeleton mechanism may be secured to the first arm by a spring housing. Additionally, the spring may be secured between a first end of the spring housing and a plunger moveable relative to the spring housing, and the cable and plunger are configured to compress the spring against the first end of the spring housing from the equilibrium position to the displaced position. The exoskeleton mechanism may further comprise a bushing disposed around the cable between the cable and the spring.

In other variations of the exoskeleton mechanism, the support arm may be connected to the first arm by an axle, and a rotary damper provided on the axle to resist movement of the support arm relative to the first arm in response to the spring force. In some arrangements, the rotary damper may be configured to be disposed proximate a pivoting joint of a user.

In yet other variations, the exoskeleton mechanism may further comprise a second arm pivotably connected to the first arm. Additionally, the exoskeleton mechanism may comprise a pivot disposed between the first arm and the second arm.

In another arrangement, an exoskeleton mechanism for supporting a joint, comprises a brace having a first arm and a support arm, the support arm pivotably connected to the first arm by an axle. The exoskeleton mechanism further includes a motor connected to the axle and coupled to the support arm via the axle. Additionally, the exoskeleton mechanism includes a sensor provided on the first arm or the support arm, the sensor configured to collect sensor data, and a controller in electrical communication with the sensor and the motor. The controller of the exoskeleton mechanism is configured to activate the motor to apply a torque via the axle on the support arm, based on the sensor data.

In some variations, the sensor may include at least one of a three-axis accelerometer and an encoder. For example, the three-axis accelerometer could be disposed on the first arm and the encoder could be disposed on the axle. Additionally, the sensor data may include at least one of acceleration data, angular position data, angular velocity data, and angular acceleration data.

In yet further arrangements, the controller may be further configured to actuate the motor in a second direction. Additionally, the exoskeleton mechanism can further include a battery, the battery in electrical communication with the controller and the motor.

Another arrangement of the present disclosure provides a method of operating a joint exoskeleton mechanism. The method includes providing a brace having a first arm and, a support arm, a controller, a sensor, and a motor. Additionally, the method includes measuring movement of the brace and angular velocity of the support arm and determining, via the controller, that the movement of the brace is below a movement threshold and the angular velocity of the support arm is above a squatting threshold. Additionally, the method includes activating the motor to provide a supporting torque.

In some variations, activating the motor to provide a supporting torque may include exerting a torque in a first direction. Additionally, movement of the brace may be measured by an accelerometer and the angular velocity of the support arm may be measured by an encoder. Further, the controller can actuate the motor to provide a resistive force using a position-current-impedance dynamic control logic.

In other variations, the method may further include determining, via the controller, that the movement of the brace is above the movement threshold, and pivoting the support arm, via the motor, to a resting position. Additionally, the method may include determining, via the controller, that the angular velocity of the brace is above a rising threshold, and activating the motor, via the controller, to move the support arm in a second direction to a resting position.

In some arrangements, the present disclosure provides an exoskeleton mechanism for supporting a joint. The exoskeleton mechanism can include a brace having a first arm and a support arm, the support arm pivotably connected to the first arm. The exoskeleton mechanism further includes a resistance element coupled with the support arm, the resistance element configured to resist angular movement of the support arm.

In some variations, the resistance element may be disposed in a housing proximate the first arm. Additionally, in the exoskeleton mechanism, the resistance element may be a spring or an electric motor. Further, the exoskeleton mechanism can include a controller in electrical communication with the motor. In other variations, the resistance element may be a damper, and the damper may be a rotary damper.

BRIEF DESCRIPTION OF THE DRAWINGS

The features of this disclosure which are believed to be novel are set forth with particularity in the appended claims. The present disclosure may be best understood by reference to the following description taken in conjunction with the accompanying drawings, in which like reference numerals identify like elements in the several figures, in which:

The figures depict preferred embodiments for purposes of illustration only and are not to scale. One skilled in the art will readily recognize from the following discussion that alternative embodiments of the systems and methods illustrated herein may be employed without departing from the principles of the invention described herein.

DETAILED DESCRIPTION

Some athletes are required to maintain a crouch stance for extended periods of time. This position, in addition to the other physical demands placed on the athlete, can cause strain on the knee joint. Over extended periods of time, the repeated strain can result in knee injury amongst professional athletes and even adolescent athletes. The strain experienced by the athlete is found to vary depending on the angle at which the knee is bent, peaking at approximately 80 degrees (where standing upright is 0 degrees). In some examples, a knee disposed at 80 degrees experiences forces as much as 1.5 times the individual's body weight. Further, an individual can feel five to seven times their body weight force in their knees when ascending from or descending into a squatting position.

In accordance with the present disclosure, a knee exoskeleton is provided that reduces strain on an athletes knee without providing an athletic advantage, where an athletic advantage is anything that assists an athlete in their physical exertions. Additionally or alternatively, the knee exoskeleton could be used in rehabilitation or physical therapy to reduce joint strain while encouraging muscle development. For example, athletic advantage would include assisting a catcher during the rising motion out of a squat. In a first example, the knee exoskeleton includes a support arm that provides support with the assistance of springs but a rotary damper to prevent any athletic advantage. In a second example, the knee exoskeleton includes an electronic controller and electric motor to provide a support torque while still not providing an athletic advantage. In both the first and second example, the knee exoskeleton can be adjusted and configured for use with male and female professional athletes as well as adolescent players.

Figure 1:
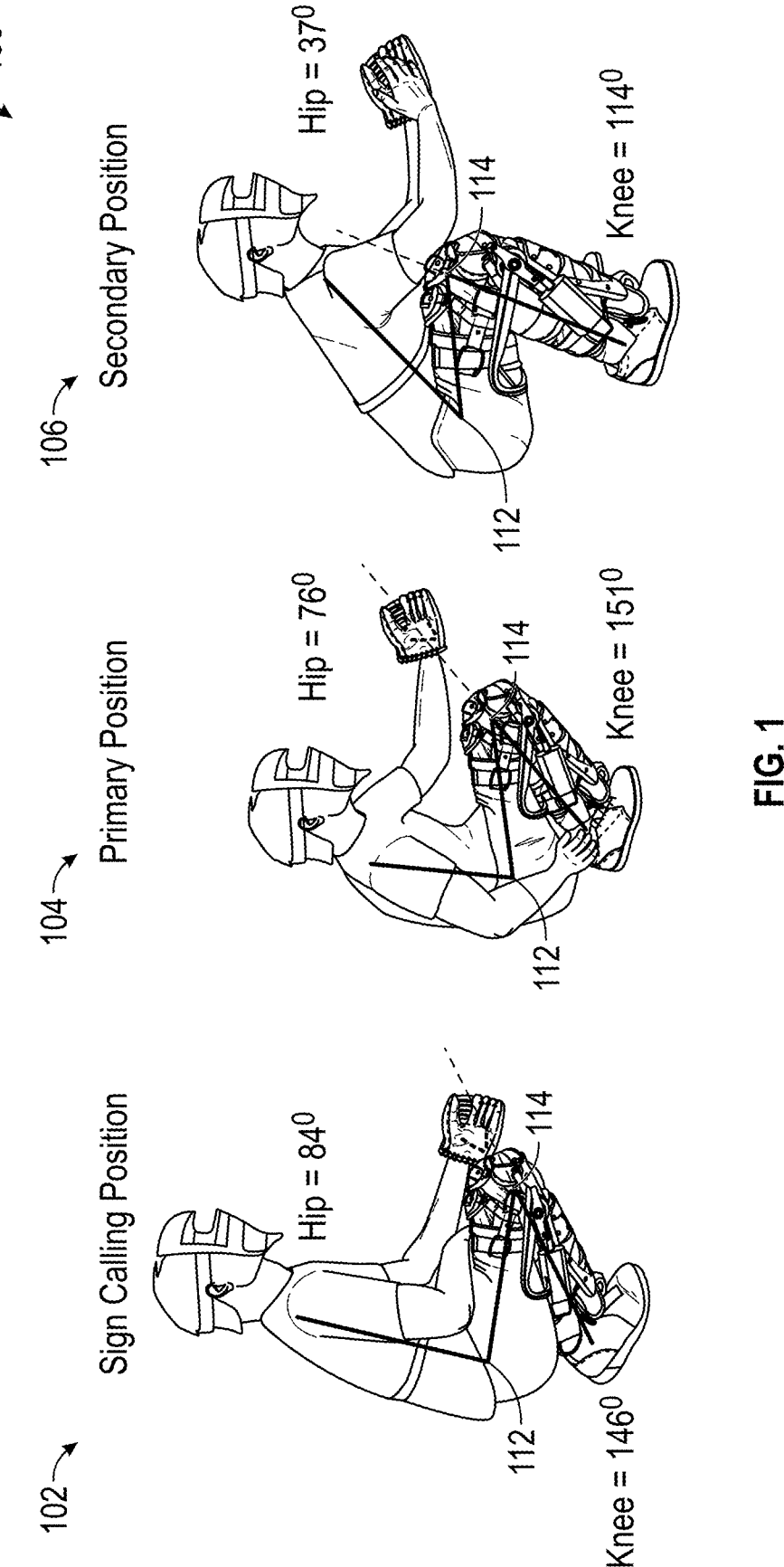
FIG. 1 is a side view of a first, second, and third catcher's stance.

FIG. 1 illustrates a catcher 100 in different positions to illustrate the angles of knee and hip joints of the catcher 100. For example, the catcher 100 is shown in a sign calling position 102, a primary position 104, and a secondary position 106, which are three variations of a crouching position that require a catcher 100 to bend at both the hips 112 and at the knees 114. Although FIG. 1 illustrates three common stances, a variety of alternative crouching stances could be used by a catcher or other athlete. In each position, the hip angle is measured relative the thigh, such that, when standing upright, the hip angle would be 180 degrees (°). Also, in each position, the knee flexion angle is measured relative the calf, such that, when standing upright, the knee flexion angle would be 0°.

The sign calling position 102 is a taller and more relaxed stance. In the sign calling position 102, the hips 112 are bent at an approximate angle of 84° while the knees 114 are bent to a knee flexion angle of approximately 146°. From the sign calling position 102, the catcher can transition to either the primary position 104 or the secondary position 106. In the primary position 104, the knees 114 are bent at approximately 114° while the hips 112 are bent at approximately 76°. However, the catcher could alternatively assume a taller, more prepared stance, such as the secondary position 106. In the secondary position 106, the hips are bent to approximately 37° and the knees are bent to approximately 114°. The secondary position 106 is useful when the catcher is concerned a player may steal a base. As a result, because the catcher might need to quickly rise from the secondary position 106, an athletic brace cannot assist the catcher in rising from the secondary position 106 because such assistance would be an unfair athletic advantage.

As can be shown from the common stances, catchers (and athletes in many sports) subject their knees 114 to highly bent positions for extended periods of time. These bent positions, and transitioning to and between these bent positions, can cause stress on the joints and varying levels of discomfort and pain.

Figure 2:
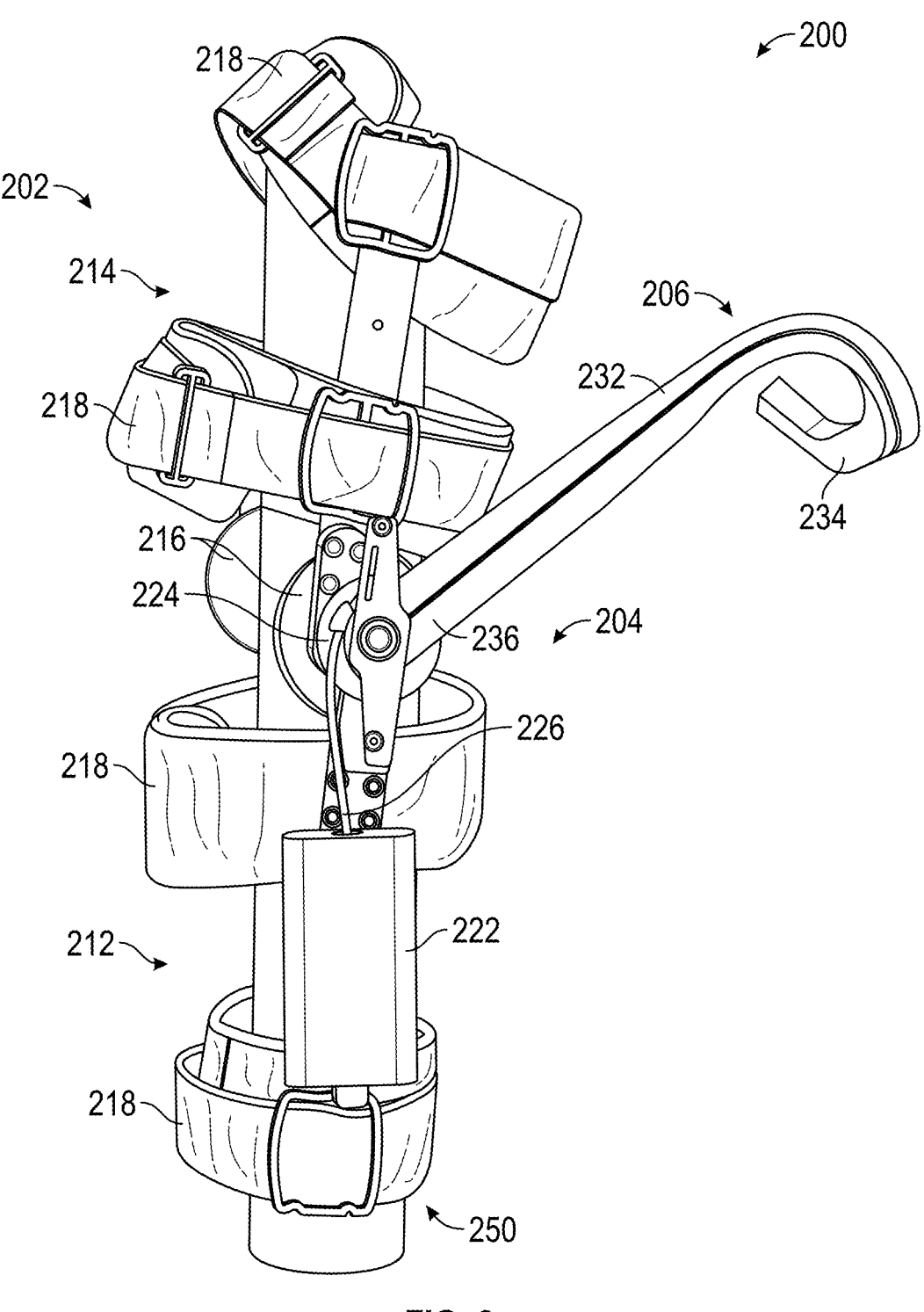
FIG. 2 is a side view of a first aspect of a catcher's knee exoskeleton in accordance with the teachings of the present disclosure.

FIG. 2 illustrates the example knee exoskeleton 200 in accordance with a first aspect of the present disclosure. The knee exoskeleton 200 includes a brace 202, a resistance element 204, and a support arm 206. The resistance element 204 is configured to resist angular movement of the support arm 206. In various embodiments, the knee exoskeleton 200 could be configured or otherwise sized for male athletes, female athletes, adolescent athletes, and child athletes.

The brace 202 of the knee exoskeleton includes a first arm 212 and a second arm 214. The second arm 214 is pivotably coupled to the first arm 212 via pivot 216. In accordance with the present example, the pivot 216 can be disposed proximate a knee such that the first arm 212 and the second arm 214 are configured to move with a calf and a thigh (respectively) of a user. The brace 202 includes a plurality of cuffs 218 made of flexible fabric and Velcro™ to secure the brace 202 to the thigh and calf of an athlete 602 (shown in FIG. 6). Alternatively, the brace 202 could include cuffs made of material other than fabric (e.g., plastic). In yet other examples, the brace 202 can be secured to the thigh and calf in any known way. For example, in some embodiments, the brace could not include the second arm 214 and only secure the knee exoskeleton to a user via the first arm 212.

The knee exoskeleton 200 further comprises the resistance element 204. In the arrangement illustrated in FIG. 2, the resistance element 204 includes a spring housing 222, a rotary damper 224, and a cable 226 coupled on either end to the spring housing 222 and the support arm 206. In various examples, the cable is coupled on either end using a swage (discussed in greater detail in FIG. 3). The rotary damper 224 is disposed proximate the pivot 216 and between the first arm 212 and the second arm 214. The spring housing 222 is disposed on the first arm 212 and includes a first and second spring 322, 324, a plunger 338, and a bushing 332 (shown in FIG. 3 and discussed in greater detail below). As a result, the springs 322, 324 are secured to the first arm 212 by the spring housing 222. The spring housing 222 is configured to exert a torque on the support arm 206 via the cable 226 when the support arm 206 is pivoted toward the first arm 212. In the knee exoskeleton 200, as shown in FIG. 2, the torque exerted by the spring housing 222 causes the support arm 206 to pivot away from the first arm 212 and towards the second arm 214.

Further, the support arm 206 includes an arm 232 and a seat portion 234. The arm 232 includes a first end 236, proximate the pivot 216 and the rotary damper 224. The arm 232 further includes an axle 512 (shown in FIG. 5) extending through the first end 236. The axle 512 rotatably couples the support arm 206 to the rotary damper 224 and pivot 216. As a result, the support arm 206 pivots relative to the resistance element 204. The seat portion 234 is disposed opposite the first end 236 of the arm 232. The seat portion 234 is pivoted, by the thigh, towards the calf when an athlete enters a crouching position.

As shown in FIG. 2, the knee exoskeleton 200 includes the resistance element 204 is disposed on a left side 250 of the brace 202. In a preferred embodiment, the knee exoskeleton 200 of FIG. 2 would be worn on a left leg of an athlete. In further preferred embodiments, a knee exoskeleton to be worn on a right leg of an athlete would include a substantially identical resistance element disposed on a right side of a brace. As such, the knee exoskeleton to be worn on left and right legs are mirrored. However, in various embodiments, the resistance element 204 can be disposed anywhere around the brace 202.

Figure 3:
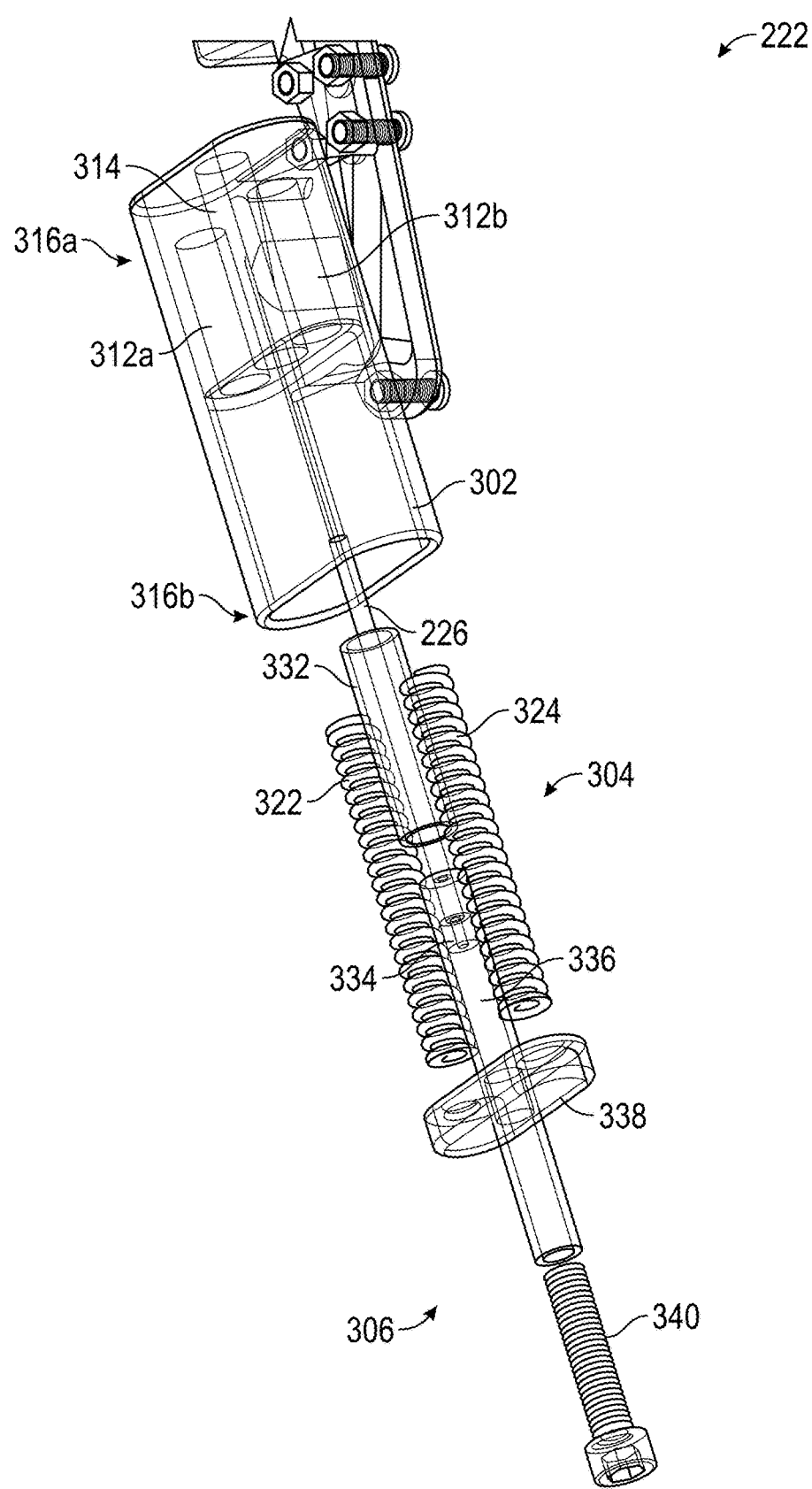
FIG. 3 is an exploded perspective view of an example spring housing of the catcher's knee exoskeleton of FIG. 2.

FIG. 3 illustrates the spring housing 222. The spring housing 222 includes the spring housing bracket 302, springs 304, and plunger mechanism 306 to retain the springs 304 in the spring housing bracket 302. The spring housing bracket 302 includes spring apertures 312a, 312b and a bushing aperture 314. The spring apertures 312a, 312b are disposed in the spring housing bracket 302 to stabilize movement of the springs 304. Further, the spring apertures 312a, 312b are disposed at a first end 316a of the spring housing bracket 302 opposite the second end 316b.

As illustrated, the springs 304 include a first spring 322 and a second spring 324. In some examples, the springs 304 may include more or fewer than two springs. For example, the spring housing 222 could be configured to have four springs to increase the spring force. Similarly, the springs could be replaced with springs having a higher spring constant. Alternatively, to reduce the spring force, the spring housing bracket 302 could be configured to have one spring or replace the springs with springs having a lower spring constant.

The plunger mechanisms 306 include a bushing 332, a swage 334, a spring guide 336, a plunger 338, and a securing mechanism 340. The plunger mechanisms 306 are mechanically secured together such that pivoting the support arm 206 (FIG. 2) causes the cable 226 to move the plunger 338 relative the spring housing 222 and pull the plunger 338 against the springs 304. The cable 226 passes through the bushing 332 and the spring guide 336 and is secured at a second end to the swage 334. The swage 334 transfers the tension force acting on the cable 226 to the plunger 338. For example, the swage 334 can directly exert a force on the spring guide 336, and the spring guide 336 can be coupled to the plunger 338 via a securing mechanism 340, such as a bolt as illustrated in FIG. 3. Additionally, the swage 334 can actuate the spring guide 336, causing the spring guide 336 to move relative the bushing 332 and the spring housing bracket 302. For example, the spring guide 336 is configured to move linearly in the bushing 332 of the spring housing bracket 302. Further, the bushing 332 can be made of a low-friction material, such as delrin and the spring guide 336 can be made of copper. In other examples, other assemblies could be implemented to transfer the compression force from the springs to exert a torque on the support arm 206 and still be within the scope of the present invention.

Figure 4:
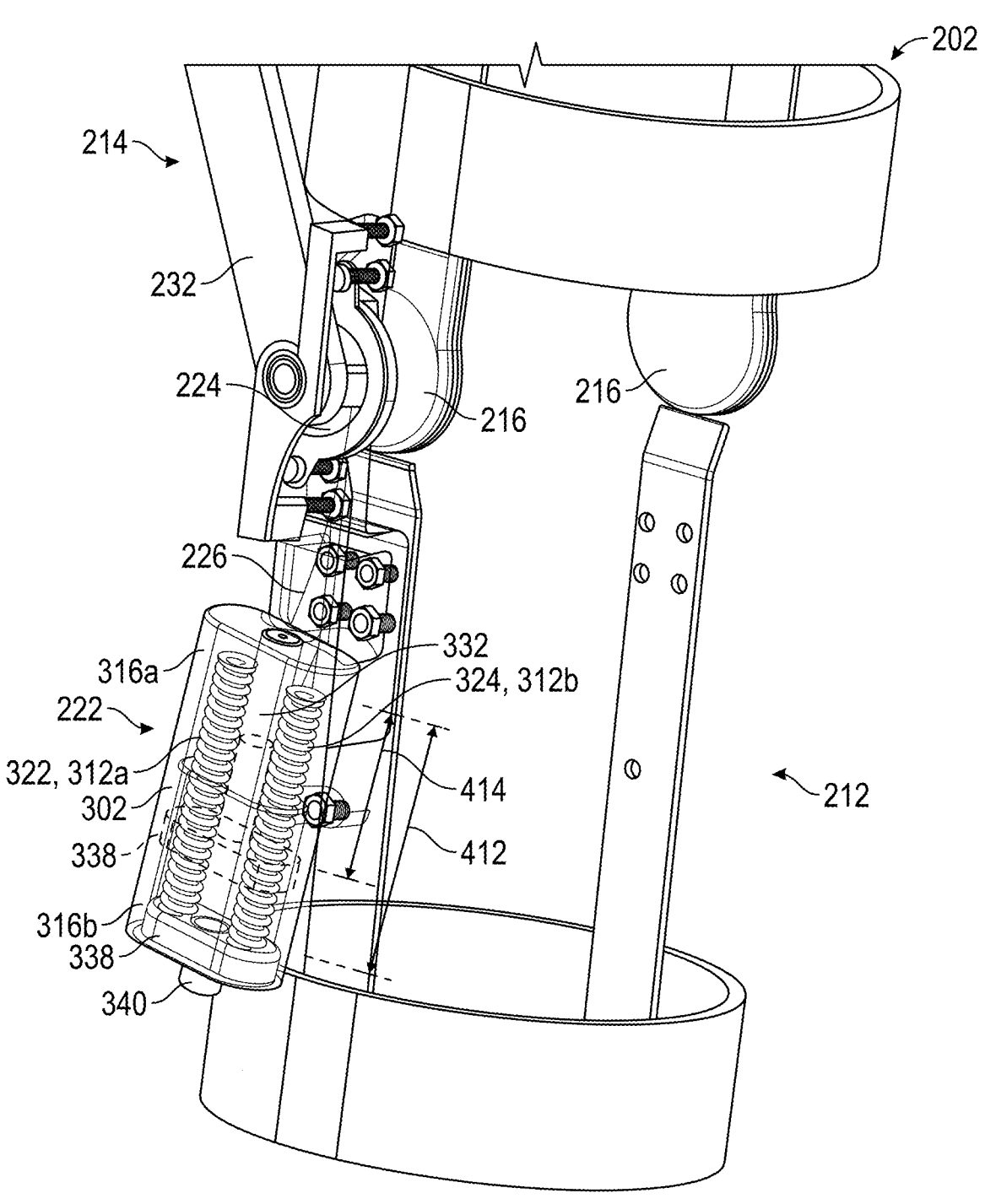
FIG. 4 is perspective view of the example spring housing of FIG. 3 disposed on a first arm of the exoskeleton of FIG. 2.

FIG. 4 illustrates the spring housing 222 of FIG. 3 properly assembled and disposed on the knee exoskeleton 200 of FIG. 2. As shown, the spring housing 222 is disposed proximate the first arm 212 of the brace 202. As assembled, the spring 322 is disposed in the spring aperture 312a against the first end 316a of the spring housing 222 and the spring 324 is disposed in the spring aperture 312b against the first end 316a of the spring housing 222. Additionally, when the arm 232 is pivoted towards the first arm 212, the cable 226 pulls the plunger 338 via the spring guide 336 towards the first end 316a. As a result, the spring 322 is compressed within the spring aperture 312a and the spring 324 is compressed into the spring aperture 312b. When the springs 322, 324 are compressed, the springs 322, 324 generate a spring force transferred to the support arm 206 via the cable 226.

As shown in FIG. 4, the springs 322, 324 can be compressed by the plunger 338. For example, the plunger 338 is disposed proximate the second end 316b such that the springs 322, 324 have a first length 412 at an equilibrium position. In the equilibrium position, the springs 322, 324 do not generate a spring force. Alternatively, when the cable 226 pulls the plunger 338, the springs 322, 324 are compressed to a second length 414 in a displaced position. In the displaced position, the springs 322, 324 generate a spring force on the plunger 338 and the first end 316a of the spring housing 222. In alternative arrangements, the springs 322, 324 could be secured to the second end 316b of the spring housing 222 and the cable 226 could be configured to pull the springs 322, 324 to have a length longer than the first length 412 at an alternative displaced position. In the alternative displaced position, the springs 322, 324 would still generate a spring force on the cable 226 and the second end 316b of the spring housing 222.

Figure 5:
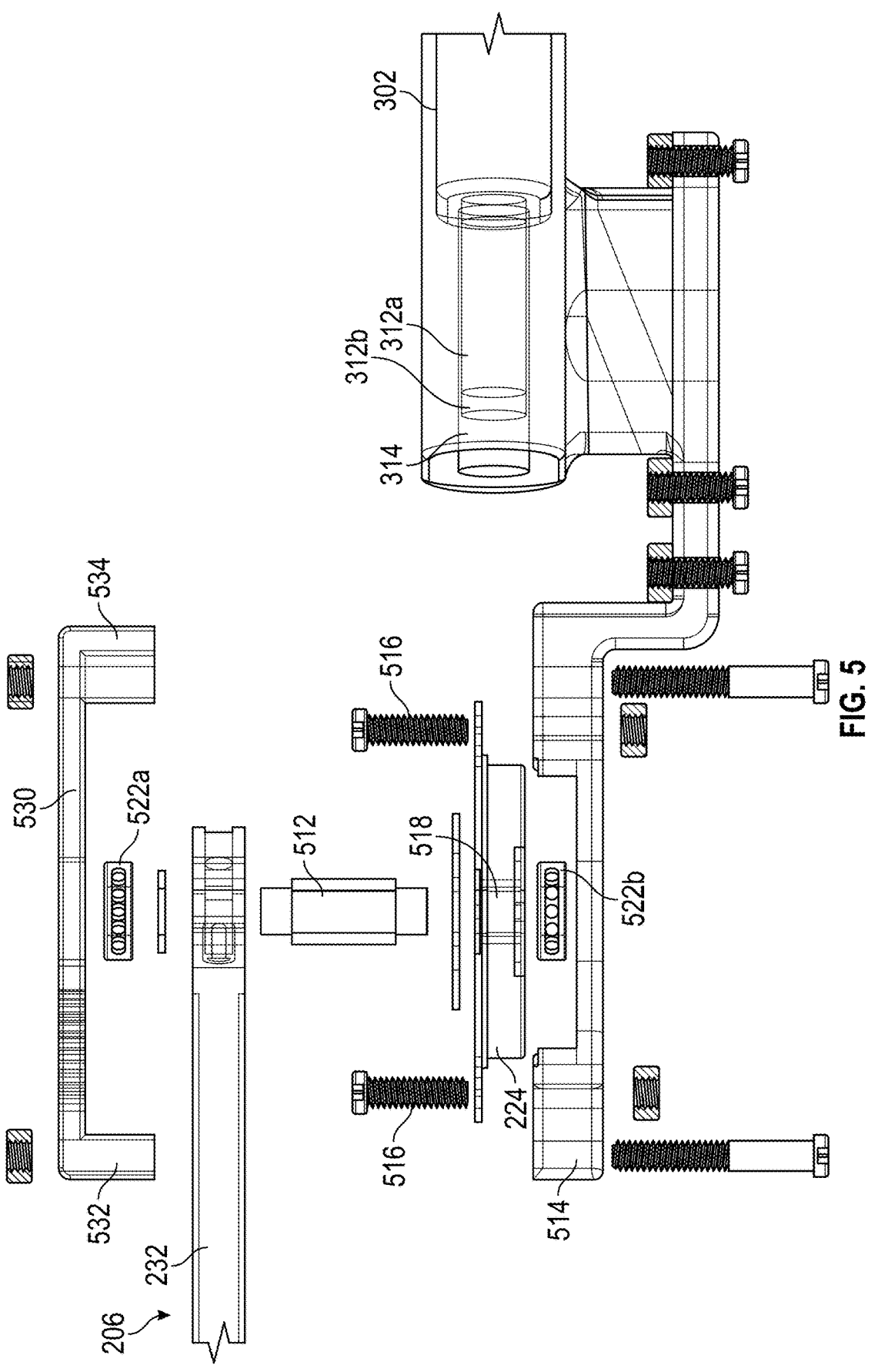
FIG. 5 is an exploded view of an example damper of the catcher's knee exoskeleton of FIG. 2.

FIG. 5 illustrates the installation of the damper 224 on the catcher's knee exoskeleton 200 of FIG. 2. The resistance element 204 of the knee exoskeleton 200 further includes the damper 224, the support arm 206, and an axle 512. The support arm 206 is pivotably coupled to the damper 224 via the axle 512.

As illustrated, the damper 224 is a rotary damper secured to the brace 514 via fasteners 516. As shown in FIG. 5, the damper 224 is a rotary damper that includes an aperture 518 to receive an axle, such as axle 512. Rotational movement of the axle 512 will be dampened because the axle 512 is coupled to the aperture 518. The rotary damper shown as damper 224 dissipates or dampens rotational energy of the axle 512 via a damping fluid. In an alternative example, the rotational movement of the axle is transformed to linear movement and the damper 224 is a linear damper, which may include a liquid or gas that dissipates energy of a piston moving in linear or reciprocating movement.

The axle 512 is coupled to the damper 224, the arm 232 and ball bearings 522a, 522b. In some examples, the axle 512 connects the support arm 206 to the first arm 212. As a result, when the arm 232 is rotated, the axle 512 additionally rotates and transmits the rotational movement to the damper 224. As a result, the damper 224, disposed on the axle 512, dampens movement of the support arm 206 relative to the first arm 212 in response to the spring force. The knee exoskeleton 200 further includes the ball bearings 522a and 522b disposed on a first end 524a and a second end 524b respectively. The ball bearings 522a, 522b assist in smooth rotation of the axle 512.

Lastly, the knee exoskeleton 200 further includes an outer bracket 530 secured to the brace 514. The outer bracket 530 includes a first arm 532 and a second arm 534. The support arm 206 is limited in movement between the first arm 532 and the second arm 534 when the outer bracket 530 is secured to the brace 514.

Figure 6:
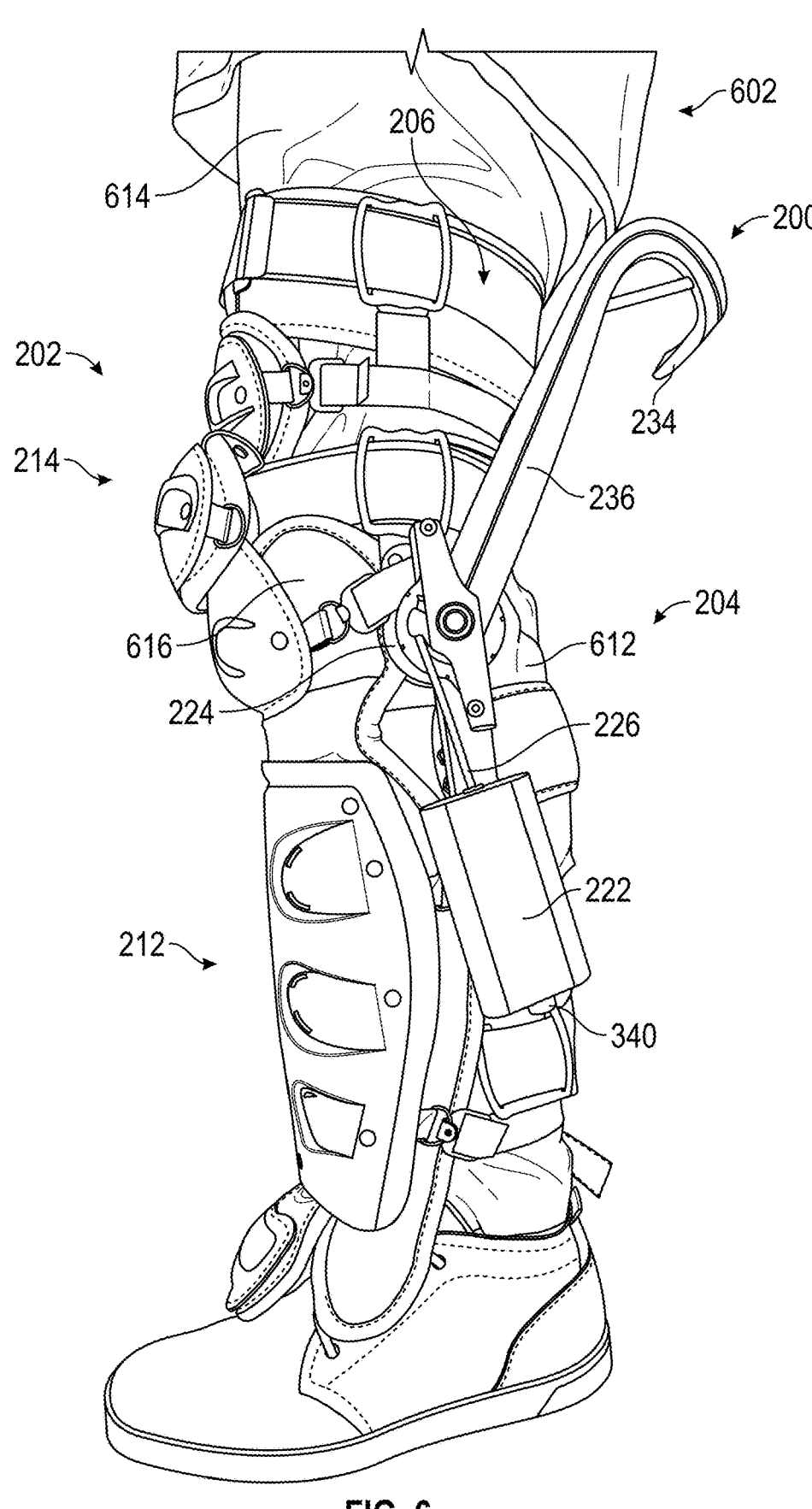
FIG. 6 is a side view of the catcher's knee exoskeleton of FIG. 2 in a first position.
Figure 7:
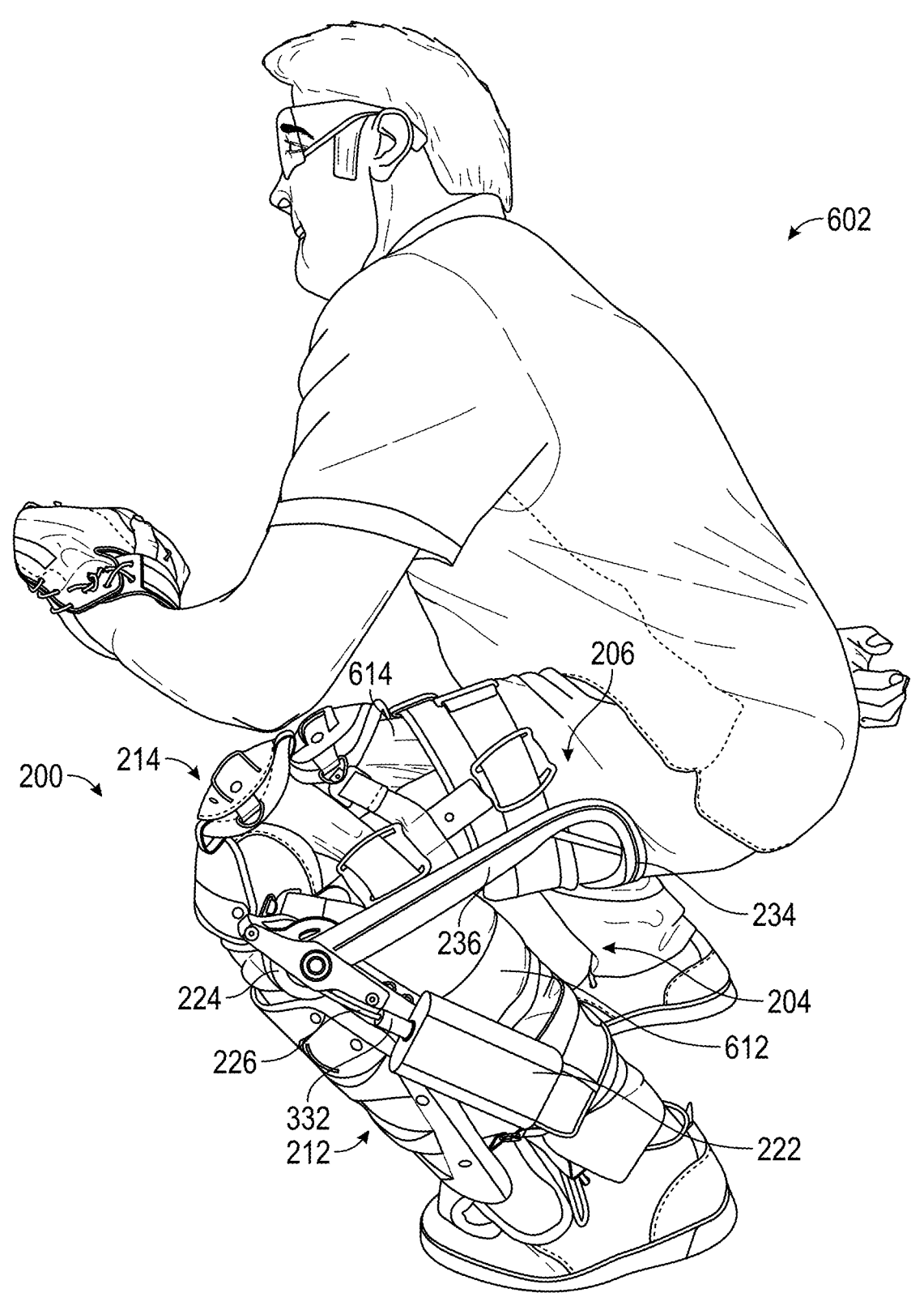
FIG. 7 is a side view of the catcher's knee exoskeleton of FIG. 2 in a second position.

FIGS. 6 and 7 illustrate the knee exoskeleton 200 disposed on an example athlete 602. The athlete 602 is standing in FIG. 6 and crouched in FIG. 7, similar to the sign calling position 102 of FIG. 1. As shown, the knee exoskeleton 200 includes the first arm 212 disposed proximate the calf 612 of the athlete 602 while the second arm 214 is disposed proximate the thigh 614 of the athlete 602. The torque exerted on the support arm 206, via the cable 226, provides a supporting force to the thigh 614 to reduce stress on the knee 616 of the athlete 602. As illustrated in FIG. 6, the support arm 206 is disposed in a resting position when the support arm is proximate the thigh and the torque exerted on the support arm 206 by gravity is balanced with the torque exerted on the support arm 206 by the springs.

As shown in FIG. 7, the cable 226 pulls the spring guide 336 partially out of the spring housing 222. As a result, the plunger 340 (shown in FIG. 6) is pulled into the spring housing 222 such that the springs 322, 324 (not shown) are compressed. As a result, the force compressing the springs 322, 324 exerts a torque on the support arm 206 via the cable 226. This torque resists the downward force exerted on the support arm 206 by the thigh of the athlete 602. Additionally, the damper 224, being a rotary damper, resists rotational movement of the support arm 206 in both directions.

When the athlete 602 stands back up, the compression force from the springs 322, 324 urge the support arm 206 to pivot upward toward the thigh 614. In the present example, the rotary damper 224 resists the angular movement of the support arm 206 in response to the torque exerted on the support arm 206 via the cable 226. As a result, when the athlete 602 quickly stands back up, the support arm 206 does not assist the athlete 602 or provide any athletic advantage. However, the support arm 206 will continue to pivot upward towards the thigh 614 until the springs 322, 324 no longer exert a torque on the support arm 206 via the cable 226.

Figure 8:
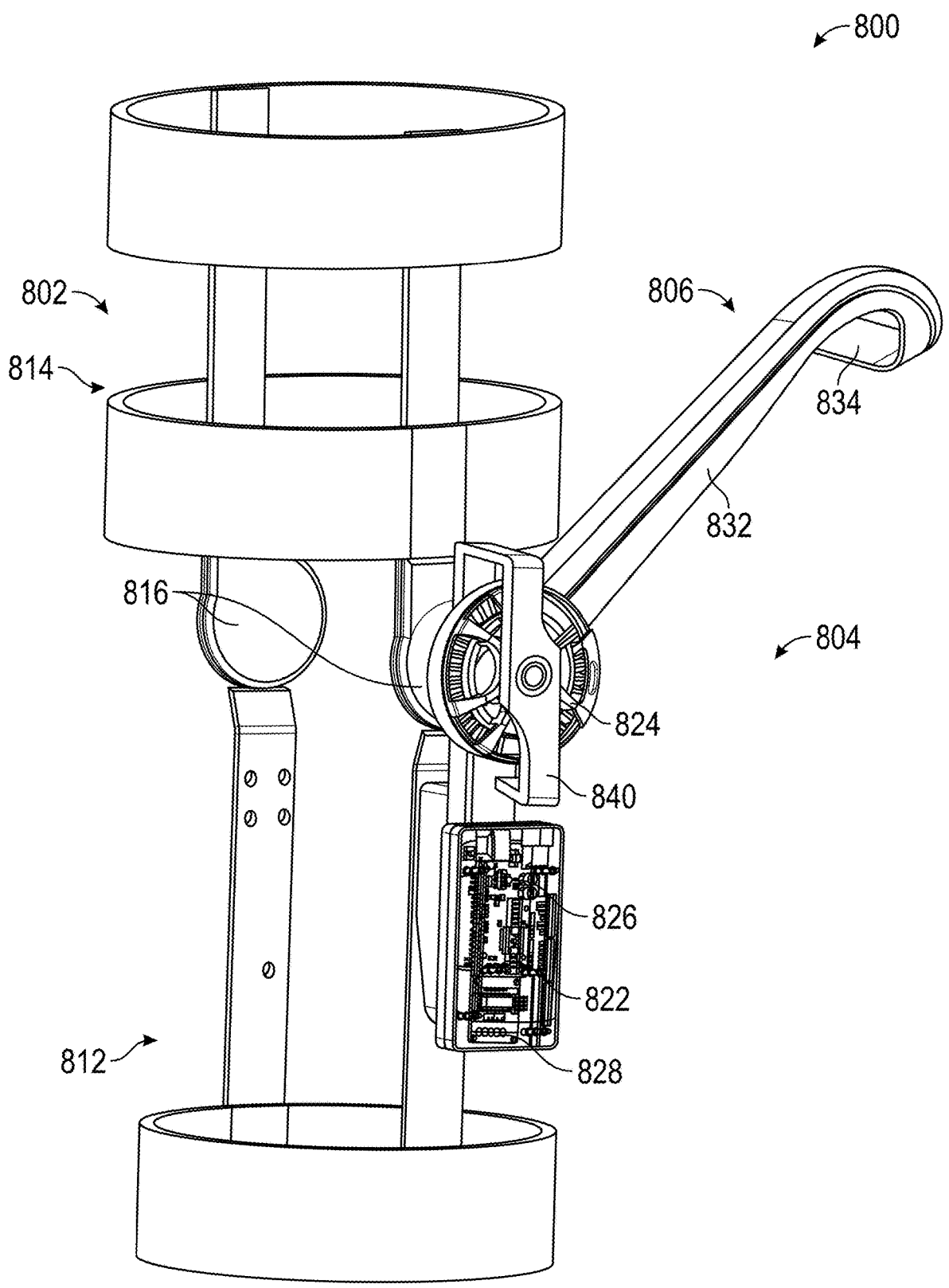
FIG. 8 is a side view of a second aspect of the catcher's knee exoskeleton in accordance with the teachings of the present disclosure.

FIG. 8 illustrates a second knee exoskeleton 800 made in accordance with the present disclosure. The knee exoskeleton 800 includes a brace 802, a resistance element 804, and a support arm 806. The brace 802 and the support arm 806 can be substantially identical to the brace 202 and the support arm 206 of FIG. 2 and operate in a substantially similar manner. For example, the brace 802 includes a first arm 812, a second arm 814, and a pivot 816 disposed between the first arm 812 and the second arm 814. Additionally, the support arm 806 includes an arm 832 and a seat portion 834.

The resistance element 804 includes a controller housing 822 and a motor 824. The motor 824 is disposed between the first arm 812 and the second arm 814, and proximate the pivot 816. Additionally, the motor 824 is coupled to the support arm 806 via an axle (not shown), similar to the axle 512 of FIG. 5. The controller housing 822 includes a control device 826, such as an Arduino™, Raspberry Pi, or similar computer device. The control device 826 is in electrical communication with the motor 824. For example, the control device 826 can be in electrical communication with an actuator driver 828 that receives a command signal from the controller, draws current from battery 912 (discussed in greater detail in connection with FIG. 9), and supplies the current to the motor. The control device 826 is configured to activate the motor 824 to exert a torque on the support arm 806 and cause the support arm to rotate or provide a supporting torque. In some examples, the resistance element 804 can include a gearbox or torque-converter. The gearbox or torque-converter can be used to amplify the torque exerted by the motor 824 on the support arm 806. As shown, the motor 824 is disposed proximate the pivot 816 of the brace 802.

Figure 9:
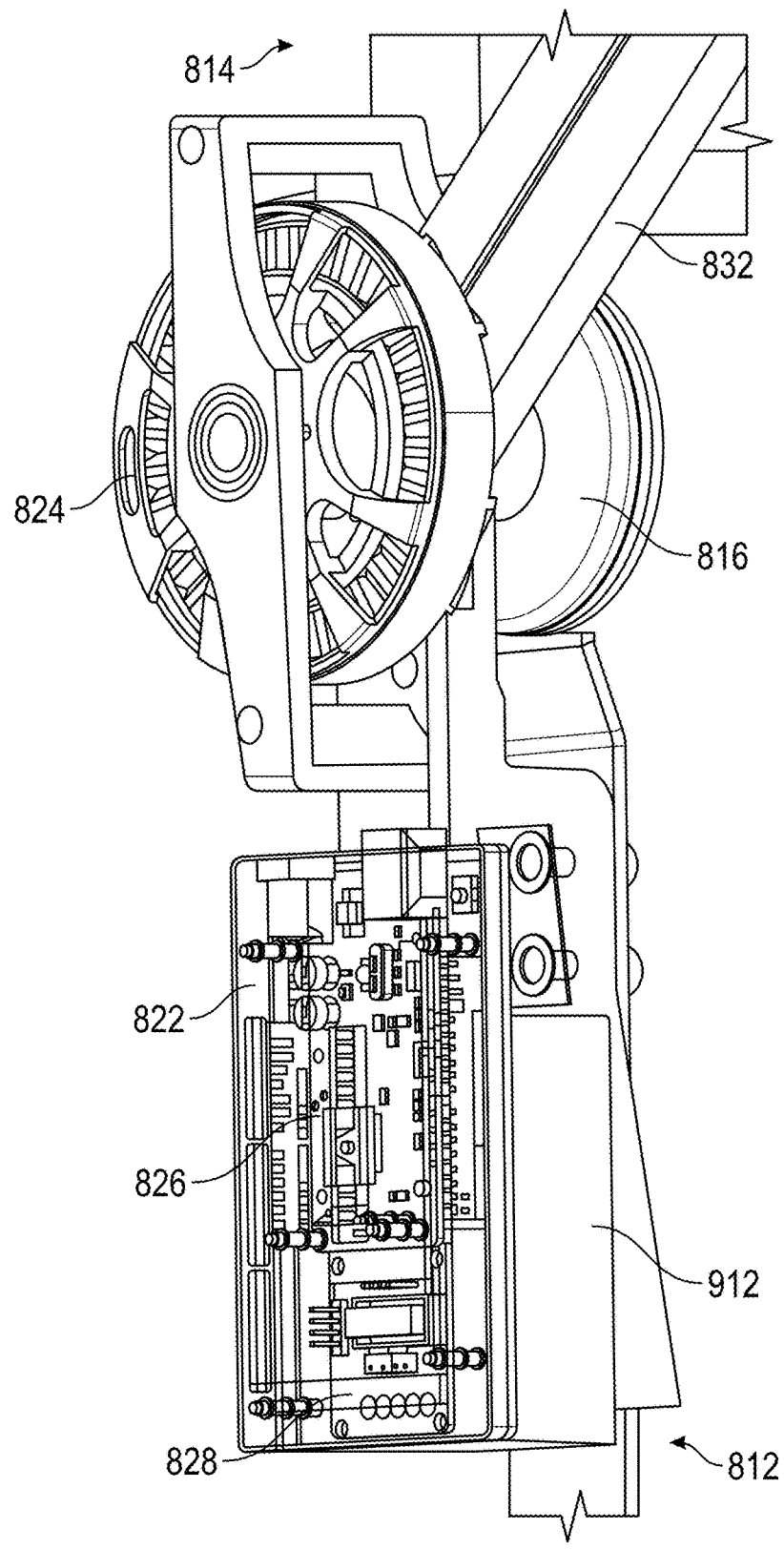
FIG. 9 is a close-up view of the catcher's knee exoskeleton of FIG. 8.

FIG. 9 also illustrates the knee exoskeleton 800 of FIG. 8. As shown in FIG. 9, the resistance element 804 further includes battery 912. The battery 912 is in electrical communication with the control device 826, the actuator driver 828, and the motor 824. As a result, the battery 912 can be configured to power both the control device 826 and the motor. In other examples, the control device 826 and the motor 824 are each provided with their own battery. In such examples, battery 912 could be a first and second battery. Additionally, the battery 912 can be rechargeable, the battery 912 can be replaced, or the battery 912 can be rechargeable batteries.

Figure 10:
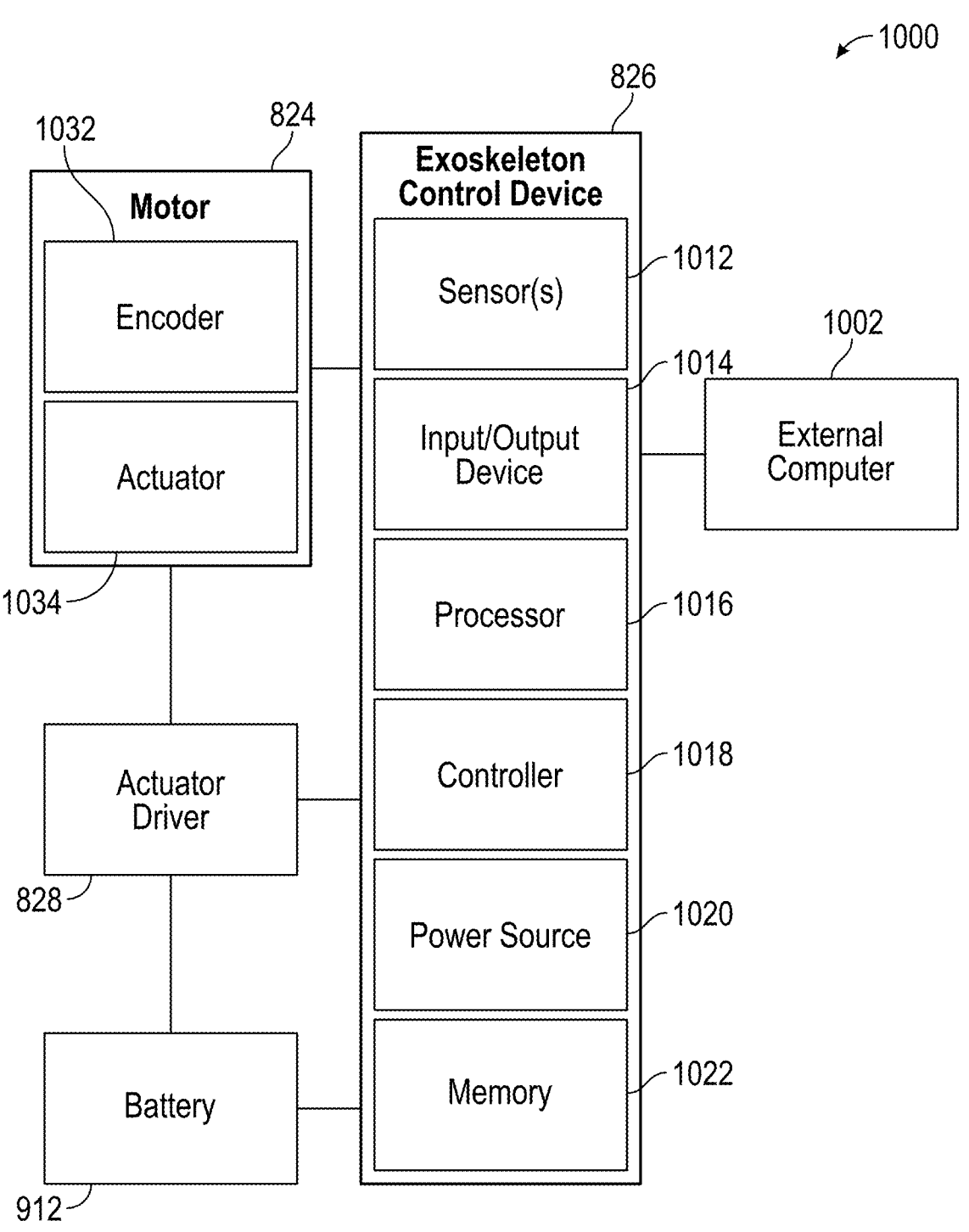
FIG. 10 is an example schematic of the knee exoskeleton system of FIGS. 8 and 9.

FIG. 10 illustrates schematically a control system 1000 of the knee exoskeleton system 800 of FIG. 8. In accordance with the present disclosure, the control system 1000 includes the exoskeleton control device 826, the motor 824, the actuator driver 828, and the battery 912. In some examples, the control system 1000 may include different components and configurations and still be considered within the scope of the present invention.

The control device 826 includes a plurality of components, including a sensor 1012, an input/output device 1014, a processor 1016, a controller 1018, a power source 1020, and a memory. Each of the plurality of components of the control device 826 are in electrical communication with the other components of the control device 826. As the control device 826 could be an Arduino™, Raspberry Pi, or similar control device, some or all of the components of the control device 826 could be integral to the control device or could be a component in electrical communication with the control device 826. For example, the sensor 1012 could include a three-axis accelerometer which is typically already incorporated in an Arduino™ or Raspberry Pi controller. In other examples, the sensor 1012 could be disposed on the first arm 812 or other component of the knee exoskeleton system 800.

The processor 1016 and the controller 1018 are utilized to receive sensor data and output commands. As illustrated, the processor 1016 and the controller 1018 are separate components of the control device 826, however in some examples, the controller 1018 can be a part of the processor 1016 and memory 1022. In some examples, the processor 1016 is a central processing unit (CPU). The processor 1016, controller 1018, and/or the memory 1022 may communicate with an external computer 1002 or the motor 824 via the input/output device 1014. In some examples, the input/output device could be a physical connection (e.g., a coaxial cable, a USB cable, an HDMI cable, etc.) or could be wireless (e.g., radio frequencies, Bluetooth, WiFi, etc.). In various examples, the external computer 1024 could include a mobile device such as a cell phone or tablet, a personal computer, or another computer.

The motor 824 includes an encoder 1032 and an actuator 1034. The actuator 1034 may include a rotor and stator having a plurality of windings configured to cause the rotor to rotate or exert a torque on an axle when the stator is properly powered. In some examples, the actuator 1034 is powered by the battery 912 and the actuator driver 828. In some examples, the actuator driver 828 could be an H-bridge or similar device for drawing current from the battery 912 and directing the current to the motor 824. The encoder 1032 is a sensor mounted on the motor 824, such as on the rotor, and the encoder 1032 is configured to detect angular displacement of the rotor. The encoder 1032 is capable of detecting the angular position and angular velocity of the support arm 832. The encoder 1032 is configured to transmit angular position, angular velocity, and/or angular acceleration data to the control device 826. In various examples, the encoder 1032 could be any sensor capable of detecting the angular position, angular velocity, and/or angular acceleration of the rotor and/or the support arm 832.

In the control system 1000 of FIG. 10, the control device 826 includes sensors 1012 and the motor 824 includes an encoder 1032. For example, the sensors 1012 includes a three axis accelerometer and the encoder 1032 is configured to detect angular position, angular velocity, and angular acceleration. In various examples, the sensors 1012 and the encoder 1032 gather various sensor data. For example, the sensor data may include acceleration data in each of three axes and angular position, velocity, and acceleration about a rotating axis. From the acceleration data, the controller 1018 and/or the processor 1016 can calculate lateral velocity, lateral acceleration, angular position, angular velocity, and angular acceleration. Accordingly, the control system 1000 can utilize sensor data to ascertain various position, velocity, and acceleration information regarding the knee exoskeleton 800.

Figure 11:
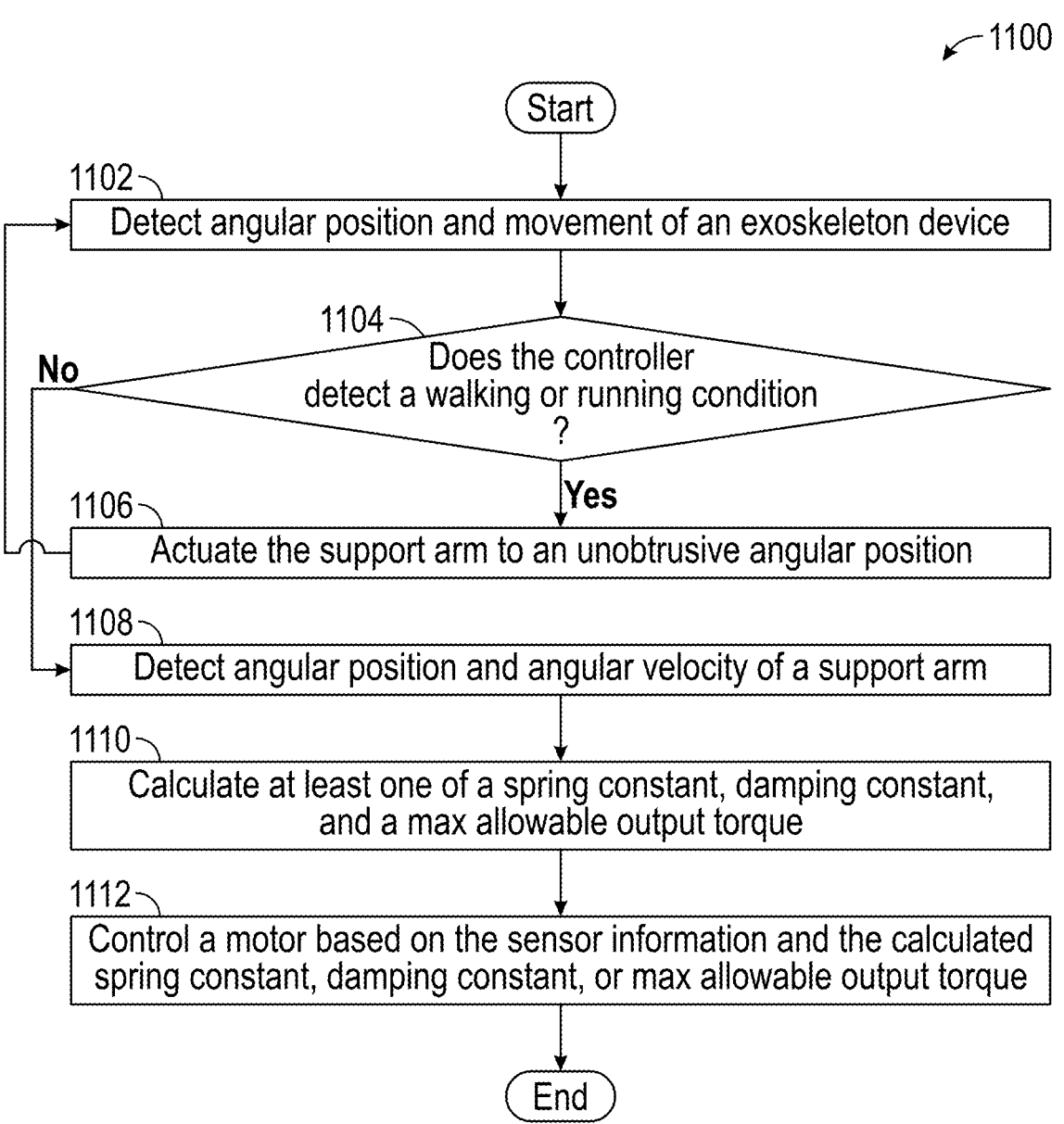
FIG. 11 is an example method of operating the example knee exoskeleton system of FIGS. 8 and 9.

FIG. 11 illustrates an example method 1100 for controlling the knee exoskeleton system 800 of FIG. 8. In various examples, the steps of the method 1100 can be rearranged or adjusted. The method 1100 begins at block 1102 when the sensors 1012 detect angular position and movement of the control device 826. For example, a three-dimensional accelerometer can detect angular position by measuring the force of gravity in a first and second axis compared to reference values. Additionally, if an athlete wearing the exoskeleton system 800 is walking or running, the sensors 1012 can detect the lateral movement of the exoskeleton system 800.

At block 1104, the controller 1018 receives data from the sensors 1012 and determines whether a walking or running condition is met. For example, the sensors 1012 may detect a pattern of acceleration data corresponding to a leg pumping when an athlete is running or walking. In such examples, the sensor may be disposed on the control device 826 or on the first arm 812 of the knee exoskeleton system 800. The acceleration data detected by the sensors 1012 and corresponding to movement of the brace 802 may exceed a movement threshold indicating the athlete 602 is running. In other examples, the control device 826 may be configured to detect the running or walking movements of an athlete in a different manner, such as detecting the pivoting of the pivot 816. If the controller 1018 detects a running or walking condition is met, the method will proceed to block 1106. At block 1106, the controller 1018 will send a command to the motor to actuate the support arm 832 to an unobtrusive angular position such as a resting position. In some examples, the controller 1018 sends the command to the motor via the actuator driver 828. In one example of the resting position, the support arm 832 is actuated to rest near or against the first arm 812. If a running or walking condition is not met, the method will proceed to block 1108.

At block 1108, the encoder 1032 detects the angular position of the support arm 832. In some examples, the support arm 832 is restricted to approximately 120 degrees (°) of movement. In such examples, the angle of the support arm 832 is considered to be zero (0) when the support arm 832 is elevated against the brace 840.

Continuing, the controller 1018 calculates at least one of a spring constant, damping constant, and max allowable output torque. In some examples, the controller 1018 calculates the spring constant, damping constant, and/or the max allowable output torque using a position-current-impedance control logic. The controller 1018 can utilize sensor 1012 data and encoder 1032 data to determine the functionality of the brace. In some examples, the function of the knee exoskeleton 800 is based, in part, on inputs provided by the athlete including height, weight, age, activity level, user preferences, and brace mode (game, practice, etc.). Additionally, the function of the brace is dictated by the information provided by the sensors 1012 and the encoder 1032. For example, the sensor 1012 and the encoder 1032 can provide information regarding whether the athlete is entering into a squatting position or leaving a squatting position. In such an example, the controller 1018 can determine the angular velocity of the support arm 806 is above a squatting threshold and activate the motor to provide a supporting torque in a first direction. In other embodiments, the sensor 1012 and the encoder 1032 can provide further information useful in controlling the function of the knee exoskeleton system 800.

Moving to blocks 1110 and 1112, the controller 1018 sends a signal to control the motor 824 based on the sensor information (e.g., data gathered by the sensors 1012 and/or encoder 1032) and the spring constant, damping constant, and/or max allowable output torque. Based on the control signal, the motor 824 can provide a torque in a first direction to support the thigh 612 of an athlete 602. The torque provided by the motor 824 can be adjusted to provide a torque adjusted based on the athlete 602 (e.g., athlete's size, weight, etc.). The torque exerted by the motor 824, ascertained based on the calculated spring constant, operates similar to the spring resistance of the knee exoskeleton 200 of FIG. 2.

Alternatively, the controller 1018 can send a signal to control the motor 824 to slowly pivot in a second direction away from the calf 612 and towards the thigh 614. This signal controls the motor 824 in a manner similar to the rotary damper 224 of the knee exoskeleton 200 of FIG. 2. The controller 1018 may provide this signal if the angular movement of the control device 826 and the angular movement of the support arm 806 each meet a threshold that satisfy the conditions for rising from a squat. In various examples, the controller 1018 can determine an athlete 602 is rising from crouching position from other sensor data.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed:

1. An exoskeleton mechanism for supporting a joint, comprising:

a brace having a first arm and a support arm, the support arm pivotably connected to the first arm by an axle;

a motor connected to the axle and coupled to the support arm via the axle;

a sensor provided on the first arm or the support arm, the sensor configured to collect sensor data;

a controller in electrical communication with the sensor and the motor, the controller having associated therewith a non-transitory memory and a processor;

based on the sensor data, the controller configured to activate the motor to apply a torque via the axle on the support arm upon the sensor collecting sensor data indicative of a condition indicative of a wearer entering a squatting position, and the controller further configured to one of deactivate the motor, and thereby discontinue applying a torque via the axle on the support arm, or activate the motor to actuate the support arm to an unobtrusive angular position, upon the sensor collecting data indicative of the wearer one of leaving a squatting position, running, or walking.

2. The exoskeleton mechanism of claim 1, wherein the sensor is at least one of a three-axis accelerometer and an encoder.

3. The exoskeleton mechanism of claim 1, wherein the sensor is a three-axis accelerometer disposed on the first arm.

4. The exoskeleton mechanism of claim 3, wherein the sensor data includes at least one of acceleration data, angular position data, angular velocity data, and angular acceleration data.

5. The exoskeleton mechanism of claim 1, wherein the controller is further configured to actuate the motor in a second direction.

6. The exoskeleton mechanism of claim 1, further comprising a battery, the battery in electrical communication with the controller and the motor.

7. The exoskeleton mechanism of claim 1, wherein the sensor is an encoder disposed on the axle.

8. The exoskeleton mechanism of claim 1, wherein the data indicative of the wearer entering the squatting position includes data indicating angular movement of the support arm exceeds a threshold satisfying angular movement consistent with the wearer entering a squat.

9. The exoskeleton mechanism of claim 1, wherein the data indicative of the wearer leaving the squatting position includes data indicating angular movement of the support arm meets a threshold satisfying conditions consistent with the wearer rising from a squat.

10. A method of operating a joint exoskeleton mechanism, comprising:

providing a brace having a first arm and, a support arm, a controller, a sensor, and a motor;

measuring movement of the brace and angular velocity of the support arm;

determining, via the controller, that the movement of the brace is below a movement threshold and the angular velocity of the support arm is above a squatting threshold; and activating the motor to provide a supporting torque.

11. The method of claim 10, wherein activating the motor to provide a supporting torque includes exerting a torque in a first direction.

12. The method of claim 10, wherein the movement of the brace is measured by an accelerometer and the angular velocity of the support arm is measured by an encoder.

13. The method of claim 10, further comprising determining, via the controller, that the movement of the brace is above the movement threshold; and pivoting the support arm, via the motor, to a resting position.

14. The method of claim 10, further comprising determining, via the controller, that the angular velocity of the brace is above a rising threshold; and activating the motor, via the controller, to move the support arm in a second direction to a resting position.

15. The method of claim 10, wherein the controller actuates the motor to provide a resistive force using a position-current-impedance dynamic control logic.

* * * * *